US009328310B1

(12) United States Patent
Deng et al.

(10) Patent No.: US 9,328,310 B1

(45) Date of Patent: May 3, 2016

(54) SUBCRITICAL WATER EXTRACTION OF LIPIDS FROM WET ALGAL BIOMASS

(71) Applicant: Arrowhead Center, Inc., Las Cruces, NM (US)

(72) Inventors: Shuguang Deng, Las Cruces, NM (US); Harvind K. Reddy, Las Cruces, NM (US); Tanner Schaub, Las Cruces, NM (US); Francisco Omar Holguin, Las Cruces, NM (US)

(73) Assignee: Arrowhead Center, Inc., Las Cruces, NM (US)

( * ) Notice: Subject to any disclaimer, the term of this patent is extended or adjusted under 35 U.S.C. 154(b) by 231 days.

(21) Appl. No.: 13/936,874

(22) Filed: Jul. 8, 2013

Related U.S. Application Data

(60) Provisional application No. 61/668,920, filed on Jul. 6, 2012.

(51) Int. Cl.
*C07C 51/43* (2006.01)
*C11B 1/10* (2006.01)

(52) U.S. Cl.
CPC ........................................ *C11B 1/10* (2013.01)

(58) Field of Classification Search
CPC ........................................................ C11B 1/10
USPC ........................................................ 554/175
See application file for complete search history.

(56) References Cited

U.S. PATENT DOCUMENTS 7,868,195 B2 1/2011 Fleischer et al.
8,409,823 B2 4/2013 Bellussi et al.
2010/0050502 A1 3/2010 Wu et al.
2011/0041386 A1 2/2011 Fleischer et al.
2011/0314881 A1 12/2011 Hatcher et al.
2012/0110898 A1 5/2012 Malm et al.
2012/0198758 A1 8/2012 Schideman et al.
2013/0079565 A1 3/2013 Miller
2013/0123469 A1 5/2013 Kumar et al.

FOREIGN PATENT DOCUMENTS

WO WO 2010021753 A1 * 2/2010
WO 2010090506 A1 8/2010

OTHER PUBLICATIONS

Chem Abstr. of CN102108302.*

Aresta, et al., "Production of Biodiesel from Macroalgae by Supercritical CO2 Extraction and Thermochemical Liquefaction", Environmental Chemistry Letters, 2005, 136-139.

Brennan, et al., "Biofuels from microalgae—A review of technologies for production, processing, and extractions of biofuels and co-products", Renewable & Sustainable Energy Reviews, 2010, 557-577.

Chakraborty, et al., "Concomitant extraction of bio-oil and value added polysaccharides from Chlorella Sorokiniana using a unique sequential hydrothermal extraction technology", Fuel, 2012, 63-70.

(Continued)

*Primary Examiner* — Deborah D Carr

(74) *Attorney, Agent, or Firm* — Isaac Estrada; Janeen Vilven; Peacock Myers, P.C.

(57) ABSTRACT

Methods of lipid extraction from biomass, in particular wet algae, through conventionally heated subcritical water, and microwave-assisted subcritical water. In one embodiment, fatty acid methyl esters from solids in a polar phase are further extracted to increase biofuel production.

48 Claims, 8 Drawing Sheets

(56) References Cited

OTHER PUBLICATIONS

Halim, et al., "Extraction of oil from microalgae for biodiesel production: A review", Biotechnology Advances, 2012, 709-732.
Harun, et al., "Bioprocess engineering of microalgae to product a variety of consumer products", Renewable & Sustainable Energy Reviews, 2010, 1037-1047.
Hu, et al., "Engineering Carbon Materials from the Hydrothermal Carbonization Process of Biomass", Advanced Materials, 2010, 813-828.
Khoo, et al., "Life cycle energy and CO2 analysis of microalgaie-to-biodiesel: Preliminary results and comparisons", Bioresource Technology, 2011, 5800-5807.
Kumar, "Microalgae to Biofuels Using Sub- and Supercritical Water Technology", Energy Technology Partnership Forum, Apr. 13, 2011.
Lardon, et al., "Life-Cycle Assessment of Biodiesel Production from Microalgaie", Environmental Science & Technology, 2009, 6475-6481.
Levine, et al., "Biodiesel Production from Wet Algal Biomass through in Situ Lipid Hydrolysis and Supercritical Transesterification", Energy & Fuels, 2010, 5235-5243.
Moeller, et al., "Subcritical Water as Reaction Environment: Fundamentals of Hydrothermal Biomass Transformation", Chemsuschem, 2011, 566-579.
Patil, et al., "Optimization of direct conversion of wet algae to biodiesel under supercritical methanol conditions", Bioresource Technology, 2011, 118-122.
Peterson, et al., "Thermochemical biofuel production in hydrothermal media: A review of sub- and supercritical water technologies", Energy & Environmental Science, 2008, 32-65.
Shuping, et al., "Production and characterization of bio-oil from hydrothermal liquefaction of microalgae Dunaliella tertiolecta cake", Energy, 2010, 5406-5411.
Toor, et al., "Hydrothermal liquefaction of biomass: A review of subcritical water technologies", Energy, 2011, 2328-2342.
Wijffels, et al., "An outlook on microalgal biofuels", Science, Aug. 13, 2010, 796-799.
Zhou, et al., "Hydrothermal Liquefaction of Macroalgae Enteromorpha prolifera to Bio-Oil", Energy & Fuels, Jun. 11, 2010, 4054-4061.

* cited by examiner

SUBCRITICAL WATER EXTRACTION OF LIPIDS FROM WET ALGAL BIOMASS

CROSS-REFERENCE TO RELATED APPLICATIONS

This application claims priority to and the benefit of the filing of U.S. Provisional Patent Application Ser. No. 61/668,920, entitled "SUBCRITICAL WATER EXTRACTION OF LIPIDS FROM WET ALGAL BIOMASS", filed on Jul. 6, 2012, and the specification and claims thereof are incorporated herein by reference.

STATEMENT REGARDING FEDERALLY SPONSORED RESEARCH OR DEVELOPMENT

This invention was made with government support under Contracts No. DE-EE0003046, FA8650-11-C-2127, awarded by the US Department of Energy, US Air Force Research Laboratory respectively, and Contracts No. EEC-1028968, MRI DBI-0520956 awarded by the National Science Foundation.

BACKGROUND OF THE INVENTION

1. Field of the Invention (Technical Field)

The present invention relates to methods of extracting lipids from biomass, and more particularly to extraction of lipids from wet algae.

2. Description of Related Art

The need for alternative energy sources to replace fossil fuels has motivated many researchers and policymakers to develop innovative research programs around the world. Development of biofuels for the transportation sector is one of those programs directed towards renewable fuels, and significant progress has been achieved in development of some renewable biofuels. Feed stocks derived from biomass are promising sources of energy as they are renewable and production of energy at the industrial scale could improve the economic prominence of both existing infrastructures and under-developed geographic resources. Biodiesel is best known among renewable fuels and is currently being produced from a wide variety of vegetable and plant oils. The implication of the utilization of vegetable oils to produce biodiesel has increased demand on the domestic markets and in some instances the production is often reduced due to scarcity of the oil. Algae have long had the attention of biofuel investigators as a new source of oil for biofuel production, since algae can produce more oil compared to other biofuel feed stocks in shorter periods of time and in smaller areas. Algae are photosynthetic organisms which utilize solar energy to grow and convert water and carbon dioxide into lipids and other metabolites. They also can be grown on waste water generated by the agricultural and food industry. Algae have been used as a source to produce a wide variety of natural products for the pharmaceutical, biomedical, and nutraceutical industries. Carbohydrates, polyunsaturated fatty acids (PUFAs), vitamins, minerals, and dietary fibers are some of the commercial products derived from algae other than oils. Development and marketing of these byproducts is crucial for sustainable production of algae biodiesel, and this strategy is widely known as "algal bio refinery". Development of byproducts during the process has become a necessary consideration to produce sustainable biofuels.

Production of algae biofuels consists of four major steps: 1) Algae cultivation, 2) Harvesting, 3) Extraction, and 4) Conversion of oils into fuels. Many different methods have been demonstrated to produce biodiesel from microalgae. These processes involve drying of algal biomass and extracting oils with expeller press, solvent extraction, etc., and some researchers have used supercritical carbon dioxide ($CO_2$) extraction of lipids to produce biofuels. The extraction of oils is the most energy intensive step among the four steps; it consumes nearly 85% of production energy in the dry extraction method. Dewatering (dehydration) is also an energy prohibitive step if the biomass is recovered with or above 20% biomass loading. Generally, it is preferable to use biomass loading between 7.5-20% for wet extraction. To reduce the energy consumption involved in extraction, wet processing methods have been explored to produce biofuels. Hydrolysis of algal biomass and conversion of hydrolyzed lipids through supercritical ethanol process and single step extraction and conversion of wet algal biomass by using supercritical methanol are examples of such methods. However, these processes are energy intensive, making the entire process less energy efficient.

In addition, to make the production of algal biofuels sustainable, valuable co-products should be recovered from the algal biomass before conversion. Chemical lysing of algae, while efficient, affects the condition of byproducts, sometimes rendering them unsuitable, for example, for consumption.

Embodiments of the present invention solve these problems by providing hydrothermal liquefaction (HTL) or subcritical water (SCW) extraction methods to extract lipids in a manner that does not detrimentally alter the production of co-products.

BRIEF SUMMARY OF THE INVENTION

Embodiments of the present invention comprise methods to extract lipids from biomass through subcritical water assisted with Microwaves, wherein the biomass comprises algae and water. In one embodiment, a method comprises feeding the biomass to a reactor, pressurizing the biomass in the reactor to a pressure that is above atmospheric pressure, heating and microwaving the biomass to heat the water to a subcritical temperature and to lyse the algae in the reactor for a residency time sufficient to lyse the algae, and separating a non-polar phase comprising lipids for bio-crude production from a polar phase comprising water and solids. One embodiment further comprises centrifuging the biomass before feeding it to the reactor to optimize water content.

Embodiments of the subcritical water assisted with microwaves method comprise loading biomass having a solids load of between approximately 0.01 dry weight percent and approximately 45 dry weigh percent, between approximately 5 dry weight percent and approximately 35 dry weigh percent, between approximately 15 dry weight percent and approximately 30 dry weigh percent, or between approximately 20 dry weight percent and approximately 28 dry weigh percent.

In one embodiment, the subcritical water assisted with Microwaves further comprises recycling the water. Embodiments of the subcritical water assisted with microwaves comprise temperatures in the reactor between approximately 160° C. and approximately 400° C., between approximately 180° C. and approximately 280° C., between approximately 195° C. and approximately 230° C., or between approximately 200° C. and approximately 210° C.

Embodiments of the subcritical water assisted with Microwaves method comprise residency times in the reactor between approximately 1 minute and approximately 60 minutes, between approximately 10 minutes and approximately 40 minutes, or between approximately 20 minutes and approximately 30 minutes. In one embodiment, the method further comprises agitating the biomass.

In one embodiment the method further comprises separating fatty acid methyl esters from the solids in the polar phase, for example, through pressurizing the biomass in a reactor to a pressure that is above atmospheric pressure and heating the biomass to heat the water to a subcritical temperature and to lyse the algae in the reactor. Heating is preferably assisted through Microwaves.

In addition, embodiments of the present invention comprise methods of lipid extraction from biomass through conventional subcritical water wherein the biomass comprises algae and water. In one embodiment, a method comprises feeding the biomass to a reactor, pressurizing the biomass in the reactor to a pressure that is above atmospheric pressure, heating the biomass to heat the water to a subcritical temperature and to lyse the algae in the reactor for a residency time sufficient to lyse the algae, separating a non-polar phase comprising lipids for biofuel production from a polar phase comprising water and solids, and separating fatty acid methyl esters from the solids in the polar phase for biofuel production. In one embodiment, the method further comprises centrifuging the biomass before feeding it to the reactor to optimize water content.

Embodiments of the conventional subcritical water method comprise loading biomass having a solids load of between approximately 0.01 dry weight percent and approximately 40 dry weigh percent, preferably between approximately 1 dry weight percent and approximately 20 dry weigh percent, and most preferably between approximately 5 dry weight percent and approximately 10 dry weigh percent.

In one embodiment, a method of conventional subcritical water further comprises recycling water. Embodiments of the conventional subcritical water comprise subcritical temperatures in the reactors between approximately 160° C. and approximately 400° C., preferably between approximately 200° C. and approximately 300° C., more preferably between approximately 210° C. and approximately 230° C., and most preferably between approximately 210° C. and approximately 230° C.

Embodiments of the conventional subcritical water comprise residency times in the reactors between approximately 1 minute and approximately 60 minutes, more preferably between approximately 10 minutes and approximately 40 minutes, and most preferably between approximately 20 minutes and approximately 30 minutes.

In one embodiment, the conventional subcritical water method further comprises separating fatty acid methyl esters from the solids in the polar phase, for example, through pressurizing the biomass in a reactor to a pressure that is above atmospheric pressure and heating the biomass to heat the water to a subcritical temperature and to lyse the algae in the reactor. Heating is optionally assisted through microwave.

Further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

DETAILED DESCRIPTION OF THE INVENTION

Water is identified as an environmentally benign, non-toxic medium with selective extraction or reaction capabilities and is a readily available "green" solvent. In one embodiment, biomass is converted into hydrothermal liquefaction (HTL) at medium temperatures (200-400° C.) and relatively high pressure, to produce a liquid product called bio-crude or bio-oil.

The reduction of the dielectric constant makes water a suitable solvent for small organic compounds, as its dielectric constant drops from 80 at room temperature to 40 at 200° C. The solubility of organic matter generally begins to increase rapidly at about 200° C. In one embodiment of the present invention, this enhanced solubility for organic compounds is accomplished through a homogeneous single-phase medium for organic synthesis in subcritical water.

In HTL, macromolecules present in the biomass are subjected to hydrolysis, which degrades them into smaller molecules. During this process, a substantial part of the oxygen in the biomass is removed by dehydration or decarboxylation. The successful use of water as a "green" solvent in previous studies indicated that SCW extraction of lipids from microalgae is an environmentally friendly alternative to traditional solvent-based extraction methods.

One embodiment of the present invention comprises SCW extraction through conventional heating. Another embodiment of the present invention comprises microwave heating, which is more selective towards neutral lipids. In another embodiment, conventional heating is used along with microwave-assisted heating in SCW for the extraction of lipids. Microwave-assisted extraction has greater selectivity towards desired compounds and a faster and better recovering capacity than traditional heating, since the resistance offered by the solution to the passing electrophoretic migration of ions of electromagnetic field causes friction between molecules resulting in the generation of heat. Along with external heat, the water inside the cell body evaporates and bursts cell walls, making extraction of cellular contents much easier.

Extraction efficiency was determined for each process by Gas chromatography-mass spectrometry (GC/MS). Produced bio-crudes were also analyzed by Fourier transform ion cyclotron resonance mass spectrometry (FT-ICR MS) for a qualitative compositional description. LEA was analyzed for nutrient value and calorific value. Thermal behavior of algae, bio-crude and pure algal oil was found through TGA.

Embodiments of the present invention comprise methods for the subcritical water extraction of algal oil from wet algal biomass wherein the algal biomass preferably has more than 90% water.

Figure 1:
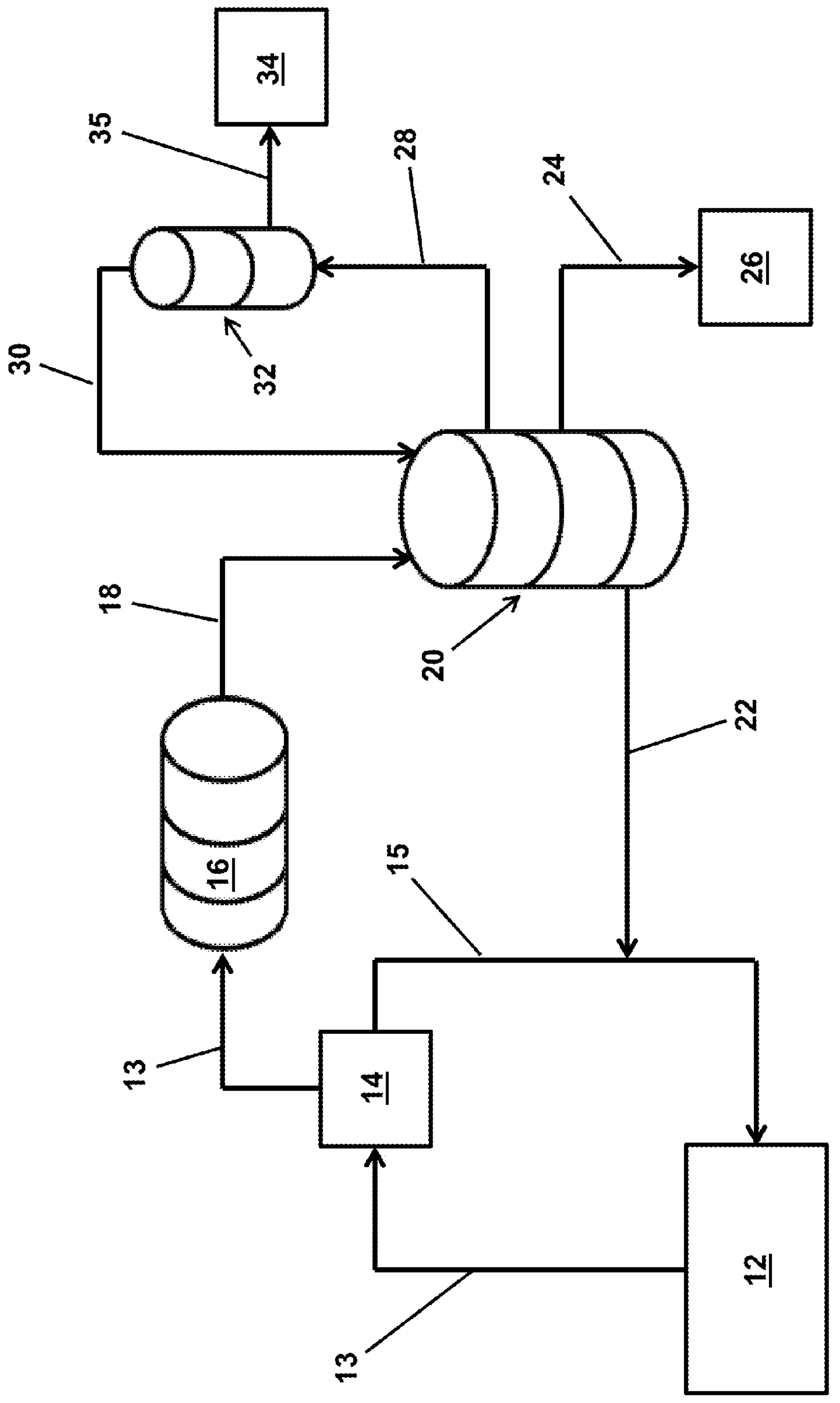
FIG. 1 is a schematic diagram for an embodiment of the present invention comprising a process protocol of subcritical water extraction from wet algal biomass.

Referring to FIG. 1, one embodiment of the present invention comprises a method of extracting lipids from a biomass, preferably wet algae. The method of this embodiment comprises mobilizing algae from source 12, which is for example an open pond. Optionally, the algae can be pumped from one destination to the next through pumping or other known methods. The water concentration of algal biomass 13 to be processed can be optimized in diverse manners, for example, through centrifuge 14, which can remove excess water 15 before the algal biomass is fed into reactor 16. Solids load is preferably optimized according to the ranges disclosed below for convention or microwave-assisted processes. Reactor 16 comprises pressure and temperature controls. In one embodiment, heating is created through conventional methods. In one embodiment, heating is created through Microwaves. In a different embodiment, conventional heating is assisted with Microwave heating. The reactor is preferably heated to an effective temperature and for a length of time ("residency time"), according to the ranges disclosed below for conventional and microwave-assisted processes. Optionally, algal biomass 13 is stirred or agitated while it is processed in reactor 16.

For conventional heating SCW, a general linear model with linear, quadratic, and cubic effects of test factors along with the interaction effects between them is preferably used to model the bio-crude yield as a function of extraction temperature, extraction time, and biomass loading for subcritical water extraction. The model is optionally expressed as:

$$\mu = \beta_0 + \sum_{i=1}^{3} \beta_i x_i + \sum_{i=1}^{3} \beta_{ii} x_1^2 + \sum_{i=1}^{2} \sum_{j=i+1}^{3} \beta_{ij} x_i x_j + \sum_{i=1}^{3} \beta_{iii} x_i^3$$

where μ is the predicted response, $x_1$, $x_2$, and $x_3$ are experimental factor levels. The model terms are included or omitted based on their significance and their impact or the lack-of-fit. The lack-of-fit of the model is insignificant with a p-value 0.38 and the overall model is significant with a p-value of 0. The parameters in the model, except the coefficient for biomass loading, are significant at 90% significance level. The model coefficients and analysis of variance are presented in Table S1a and Table S1b below.

TABLE S1a

Estimated regression coefficients for bio-crude yield using conventional heating SCW extraction method

| Term | Coef | SE Coef | T | P | Significant |
|---|---|---|---|---|---|
| Constant | −1308.7 | 208.263 | −6.284 | 0 | Yes |
| Temp | 17.33 | 2.978 | 5.819 | 0 | Yes |
| Time | 0.88 | 0.452 | 1.940 | 0.074 | Yes |
| Biomass | 1.76 | 1.357 | 1.297 | 0.217 | No |
| Temp*Temp | −0.07 | 0.014 | −5.273 | 0 | Yes |
| Time*Biomass | −0.1 | 0.058 | −1.786 | 0.098 | Yes |
| Temp*Temp* Temp | 0 | 0 | 4.783 | 0 | Yes |

TABLE S1b

Analysis of variance for bio-crude yield using conventional heating SCW extraction method

| Source | DF | Seq SS | Adj SS | Adj MS | F | P |
|---|---|---|---|---|---|---|
| Regression | 6 | 1816.17 | 1816.17 | 302.69 | 31.521 | 0.000 |
| Temp | 1 | 468.79 | 325.2 | 325.20 | 33.864 | 0.000 |
| Time | 1 | 6.93 | 36.15 | 36.15 | 3.764 | 0.074 |
| Biomass | 1 | 29.46 | 16.16 | 16.16 | 1.683 | 0.217 |
| Temp*Temp | 1 | 1060.68 | 266.97 | 266.97 | 27.801 | 0.000 |
| Time*Biomass | 1 | 30.62 | 30.62 | 30.62 | 3.188 | 0.098 |
| Temp*Temp* Temp | 1 | 219.69 | 219.69 | 219.69 | 22.877 | 0.000 |
| Error | 13 | 124.84 | 124.84 | 9.60 | | |
| Lack-of-Fit | 8 | 85.65 | 85.65 | 10.71 | 1.366 | 0.381 |
| Pure Error | 5 | 39.19 | 39.19 | 7.84 | | |
| Total | 19 | 1941 | | | | |

The maximum bio-crude yield is obtained at extraction temperature preferably between approximately 160° C. and approximately 400° C., more preferably between approximately 200° C. and approximately 300° C., and most preferably between approximately 210° C. and approximately 230° C. For conventional heating SCW, bio-crude yield increases when the biomass loading (percent by weight of biomass/weight of water) decreases. The decrease in biomass loading increases the water content in the extraction process, which in turn requires higher energy for heating the biomass to the extraction temperature. For this reason, biomass loading is preferably between 0.01 dry weight percent and approximately 40 dry weigh percent, more preferably between 1.0 dry weight percent and approximately 20 dry weigh percent, and most preferably between 5 dry weight percent and approximately 10 dry weigh percent. In one embodiment the residency time is between approximately 1 minute and approximately 60 minutes, more preferably between approximately 10 minutes and approximately 40 minutes, and most preferably between approximately 20 minutes and approximately 35 minutes. In one embodiment pressure in reactor 16 is maintained at between approximately 6 and approximately 221 bar, more preferably between approximately 15 and approximately 83 bar, and most preferably between approximately 18 and approximately 26 bar. One embodiment of the present invention comprises, for example, process conditions fixed at about 220° C. extraction temperature, 7.5 percent biomass loading, and 25 minutes extraction time under a pressure of 24.5 bar.

For microwave-assisted SCW, a general linear model with linear and quadratic effects of experimental factors is preferably used to model the bio-crude yield as a function of extraction temperature, extraction time, and biomass loading for microwave-assisted subcritical water extraction. The model is optionally expressed as, $$\mu = \beta_0 + \sum_{i=1}^{3} \beta_i x_i + \sum_{i=1}^{3} \beta_{ii} x_1^2$$

where μ is the predicted response, $x_1$, $x_2$, and $x_3$ are experimental factor levels.

The overall model is significant with a p-value of 0.001. All the parameters in the model are significant at 90% significance level. The model coefficients and analysis of variance are shown in Table S2a and Table S2b below.

TABLE S2a

Estimated regression coefficients for bio-crude yield using MW-SCW extraction method

| Term | Coef | SE Coef | T | P | Significant |
|---|---|---|---|---|---|
| Constant | −282.08 | 117.363 | −2.403 | 0.04 | Yes |
| Temp | 2.494 | 1.187 | 2.101 | 0.065 | Yes |
| Time | 2.728 | 0.633 | 4.31 | 0.002 | Yes |
| Biomass | 2.398 | 0.802 | 2.991 | 0.015 | Yes |
| Temp*Temp | −0.006 | 0.003 | −1.997 | 0.077 | Yes |
| Time*Time | −0.056 | 0.015 | −3.666 | 0.005 | Yes |
| Biomass* Biomass | −0.046 | 0.019 | −2.457 | 0.036 | Yes |

TABLE S2b

Analysis of variance for bio-crude yield using MW-SCW extraction method

| Source | DF | Seq SS | Adj SS | Adj MS | F | P |
|---|---|---|---|---|---|---|
| Regression | 6 | 528.124 | 528.124 | 88.021 | 10.56 | 0.001 |
| Linear | 3 | 329.541 | 263.114 | 87.705 | 10.52 | 0.003 |
| Temp | 1 | 110.562 | 36.783 | 36.783 | 4.41 | 0.065 |
| Time | 1 | 150.668 | 154.811 | 154.811 | 18.57 | 0.002 |
| Biomass | 1 | 68.311 | 74.573 | 74.573 | 8.95 | 0.015 |
| Square | 3 | 198.582 | 198.582 | 66.194 | 7.94 | 0.007 |
| Tem p*Temp | 1 | 34.712 | 33.226 | 33.226 | 3.99 | 0.077 |
| Time*Time | 1 | 113.559 | 112.049 | 112.049 | 13.44 | 0.005 |
| Biomass* Biomass | 1 | 50.312 | 50.312 | 50.312 | 6.04 | 0.036 |
| Residual Error | 9 | 75.018 | 75.018 | 8.335 | | |
| Total | 15 | 603.142 | | | | |

Accordingly, maximum bio-crude yield for microwave-assisted SCW is obtained at extraction temperature preferably between approximately 160° C. and approximately 400° C., more preferably between approximately 180° C. and approximately 280° C., and most preferably between approximately 200° C. and approximately 210° C. While the heat transfer mechanism in conventional heating depends on the thermal conductivity of the sample and solvent and convective currents make it a slow process, microwave heating is faster due to the volumetric heating. Thus, for microwave-assisted SCW, the yield of bio-crude is increased with increasing biomass loading. Biomass loading thus is preferably between 0.01 dry weight percent and approximately 45 dry weigh percent, more preferably between 5 dry weight percent and approximately 35 dry weigh percent, and most preferably between 15 dry weight percent and approximately 30 dry weigh percent. In one embodiment the residency time is between approximately 1 minute and approximately 60 minutes, more preferably between approximately 10 minutes and approximately 40 minutes, and most preferably between approximately 20 minutes and approximately 35 minutes. In one embodiment pressure in reactor 16 is maintained at between approximately 6 and approximately 221 bar, more preferably between approximately 15 and approximately 83 bar, and most preferably between approximately 18 and approximately 26 bar. In one embodiment, a process comprises, for example, 205° C. as extraction temperature, 25% biomass loading and 25 minutes at a pressure of 21.5 bar.

In one embodiment of the present invention, reactor 16 is optionally cooled and effluent 18 is preferably transferred to separation unit 20, where lipid globules 28 are separated from water 22 and LEA 24 (lipid extracted algae). In one embodiment, lipid globules 28 are separated by adding solvent 30 to effluent 18, wherein solvent 30 is preferably a non-polar solvent, and more preferably hexane. Mixture 28, comprising solvent and lipid globules, is preferably separated and transferred to solvent recovery unit 32. LEA 24 is optionally centrifuged to remove water 22. Water 22 is optionally recycled, preferably to back to source 12. In one embodiment, water 22 carries nutrients and other compounds that are harvested for commercial applications. LEA 24 is preferably harvested for production of byproduct 26. Optionally, LEA 24 is further processed to separate fatty acid methyl esters (FAME) in it for biofuel production. Residual FAME content in the LEA can be utilized through methods including, but not limited to, conventional combustion, pyrolysis, gasification and an additional step of subcritical water extraction at different conditions. Combustion of LEA converts the FAME and other energy-containing components in LEA into thermal energy, pyrolysis produces both liquid and gas fuels from LEA, and gasification mainly produces gaseous fuel from LEA. In one embodiment, FAME in LEA is separated through another step of subcritical water extraction comprising higher temperatures, preferably between approximately 250° C. and 450° C., and more preferably between approximately 300° C. and approximately 400° C.; and higher pressures, preferably between approximately 60 and 250 bar, but more preferably between 80-200 bar.

In one embodiment, algal bio-crude 35 is optionally transferred to bio-refinery 34, while solvent 30 is preferably reused in separation unit 20. In one embodiment, a rotary evaporator is optionally operated under vacuum to remove solvent 30 from bio-crude 35.

INDUSTRIAL APPLICABILITY

The invention is further illustrated by the following non-limiting examples.

Example 1

Response surface methodology is a statistical method used for optimizing the independent variables for maximum or minimum response. In this work, the independent variables are the following: extraction temperature (° C.), biomass loading (%-wt. of biomass/wt. of water), and extraction time (min). After finishing the tests, a suitable mathematical model was developed to predict the response based on the testsfactors. A 90% significance level was used to select the model terms. Complete analysis of variance (ANOVA) was done using Minitab v16.1.0 and the contour plots explaining the response surface were obtained using Matlab v7.12.0.635 (R2011a).

There was no extraction achieved at temperatures below 160° C. The bio-crude yield increased as the temperature was increased to 240° C., but byproducts started degrading to undesirable compounds in the extracted bio-crude. Hence a temperature range between 160° C. and 240° C. was used for optimizing the C-SCW extraction process. The C-SCW extraction experiments were conducted with *N. salina* algal biomass procured from Solix biofuels to obtain the optimum conditions for maximum extraction. Freshly cultured, harvested *N. salina* algal biomass was used for microwave-assisted extraction experiments and Folch extraction. The same biomass was used to perform experiments of C-SCW at optimum extraction conditions for comparison of extraction efficiency with MW-SCW extraction experiments at optimized conditions and Folch extraction. Due to limitations in operating conditions of the microwave, the microwave-assisted subcritical water experiments were conducted between the temperature range 160° C. and 220° C. Preliminary studies indicated that maximum bio-crude yield was achieved during an extraction time from 15 to 30 min. Circumscribed central composite design was used to design the experiments between the experimental factors such as extraction temperature, extraction time, and biomass loading at three levels; low (−1), central (0), and high (1). This type of central composite design uses points outside the design space (−1.68, 1.68 levels) which provides a good estimate over the entire design space. There were a total of 20 experiments as shown in Table 1 for conventional subcritical water extraction and 16 experiments for microwave-assisted subcritical water extraction, which were completely randomized to eliminate any systematic errors.

TABLE 1

Conventional heating subcritical water extraction

| Exp. run | Temp | Extraction Time (min.) | Biomass loading | Yield (%) of bio crude(dry wt. basis) |
|---|---|---|---|---|
| 1 | 215.00 | 9.89 | 7.50 | 45.84 |
| 2 | 180.00 | 30.00 | 5.00 | 42.44 |
| 3 | 215.00 | 22.50 | 7.50 | 49.82 |
| 4 | 273.86 | 22.50 | 7.50 | 39.70 |
| 5 | 215.00 | 22.50 | 7.50 | 46.21 |
| 6 | 180.00 | 15.00 | 5.00 | 33.60 |
| 7 | 250.00 | 15.00 | 5.00 | 41.08 |
| 8 | 180.00 | 15.00 | 10.00 | 38.56 |
| 9 | 215.00 | 22.50 | 11.70 | 42.85 |
| 10 | 215.00 | 22.50 | 3.30 | 54.96 |
| 11 | 156.14 | 22.50 | 7.50 | 3.95 |
| 12 | 180.00 | 30.00 | 10.00 | 36.65 |
| 13 | 215.00 | 22.50 | 7.50 | 45.06 |
| 14 | 250.00 | 30.00 | 10.00 | 42.04 |
| 15 | 215.00 | 22.50 | 7.50 | 45.90 |
| 16 | 215.00 | 22.50 | 7.50 | 42.42 |
| 17 | 215.00 | 22.50 | 7.50 | 49.50 |
| 18 | 250.00 | 15.00 | 10.00 | 44.10 |
| 19 | 250.00 | 30.00 | 5.00 | 43.92 |
| 20 | 215.00 | 35.11 | 7.50 | 47.04 |

*N. salina* algal biomass was received from two sources. Moisture content was 62% and 63% for respective biomasses in the above stated order and both were harvested by centrifugation. All solvents used in this study were analytical grade reagents.

A stainless steel bench top reactor accompanied by a controller unit was used for conventional heating extraction experiments. The microwave-assisted subcritical water extraction experiments were performed in a microwave reactor (operating parameters: 0-60 bar, 25-220° C., 0-1400 W, 10-60 mL/Teflon tube reactor with 16 tubes) enclosed with a specially designed rotor. Both reactors were equipped with pressure gauges. A scanning electron microscope equipped with an energy-dispersive X-ray spectrometer (EDS) was used for elemental analysis of algal biomass.

Imaging of thin sections of algae was carried out with a transmission electron microscope. Thermo gravimetric analysis (TGA) of wet algal biomass was performed. A gas chromatograph with a 5972a mass selective detector equipped with a capillary column DB-23, 30 mm×0.25 mm diam.×0.25 μm film was used for fatty acid methyl ester analysis. Compositional analysis of intact lipids was performed for lipid extracts by direct infusion into a hybrid linear ion trap FT-ICR mass spectrometer equipped with an automated fraction collection and nanoelectrospray system.

Conventional Lipid Extraction

Conventional lipid extraction was performed by the Folch method (Folch et al., 1957). For this procedure, dried algal samples (0.1 g) were extracted in triplicate for 30 min with 2 mL of chloroform/methanol (2:1 v/v) at 25° C. with continual vortexing. Extracts were centrifuged and the supernatant removed. Extraction was repeated and combined supernatants were evaporated in pre-weighed vials under a steam of nitrogen. All lipid extracts were stored under nitrogen at −20° C. for FT-ICR MS analysis.

FAME (fatty acid methyl esters) analysis was performed by direct methylation of 50 mg of dry tissue or bio-crude which was weighed and placed in 12 mL glass tube. Next, 10 μL of glycerol tritridecanoate (13:0 FAME standard at 20 mg/mL in hexane) was added as internal standard to each sample vial. Then 5 mL of 0.2 N KOH in MeOH was added and each sample was vortexed for 20 seconds. These samples were placed in a hot water bath at 65° C. for ten minutes and vortexed for 30 seconds. These last two steps were repeated three times total. To stop the reaction, 1 mL of 1M acetic acid was added to each sample and then each sample was vortexed for 20 seconds. Two mL of hexane with internal standard (methyl tricosanoate at 50 mg/L in hexane) was added to each sample vial. Each sample was vortexed for 20 seconds and two phases were separated by centrifugation. The top hexane layer was taken for the GC-MS analysis. Helium was used as the carrier gas with a 2 μl injection volume. The temperature ramp started at 80° C. and ramped at 20° C./min to 220° C. and held for 6 minutes for a total run time of 13.3 minutes. The instrument was tuned with a standard spectra auto tune method, and a calibration curve was made from a Supelco 37 Comp. FAME mix 10 mg/ml in $CH_2Cl_2$. Total lipid was determined gravimetrically by the Folch method and the lipid profile determined by FAME analysis as described above. For analysis of elemental composition, algal biomass samples and lipid extracted algae samples were washed with deionized water, air-dried, and then mounted on adhesive carbon tabs on aluminum sample stubs as a monolayer of powder particles. Elemental spectra of biomass particles were collected at 15 kV using the SEM-EDS microanalysis system.

Samples were analyzed by direct infusion mass spectrometry performed with a hybrid linear ion trap FT-ICR mass spectrometer. Algal lipid extracts were prepared by dissolution in methanol:chloroform (1:2 v/v) for a normalized concentration of 10 mg/mL. These stock solutions were further diluted 200 fold into 1 mL of 2:1 methanol:chloroform for a final concentration of 0.05 mg/mL, which contained 5 μL of aqueous 1 M sodium acetate (positive ion mode) or 1 M ammonium hydroxide (negative ion mode) and 10 μg/mL of phosphatidylethanolamine, PE(17:0/17:0), as an internal standard. All solvents used were high-performance liquid chromatography (HPLC) grade. Sample introduction was performed with an Advion Triversa NanoMate. Data was collected at a mass resolving power of $m/\Delta m_{50\%}$=400,000 (m/z 400) and 150 time domain transients were co-added prior to fast Fourier transformation and frequency to m/z conversion. Elemental compositions were assigned and searched against a list of lipids derived from the Lipid Maps database.

A constant volume of feed (80 mL for conventional and 60 mL for MW-SCW) was used with varying biomass loading. Samples were prepared according to the biomass loading by adding sufficient deionized water. Then the samples were fed into the reactor or reactor tubes, and the temperature maintained as per the experimental plan. The reactors were cooled down after completion of the experiment, and all the product mixture was transferred into a separation funnel and 15 mL of n-hexane was added. Five mL of n-hexane was used to wash the agitator to free any bio-crude globules adhered to it and then was transferred to the separation funnel. The mixture was thoroughly stirred with disposable spatula and then left for 15 min to settle. The water layer was collected for the material balance measurements and the hexane layer containing bio-crude and LEA was transferred to centrifuge tubes.

Figure 6:
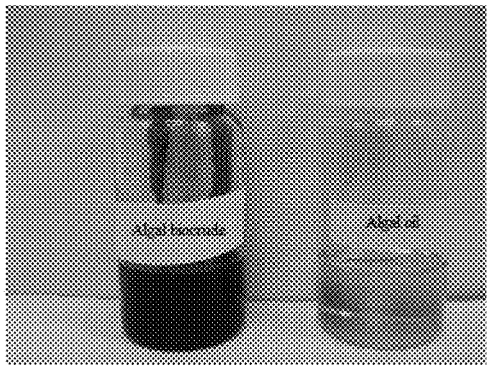
FIG. 6 shows a photograph of algal bio-crude and pure algal oil.

Bio-crude and LEA biomass were separated in centrifuge tubes, which were operated at 3200 rpm for 5 min. The less dense hexane layer, which contained lipids, was separated from LEA and transferred into a pre-weighed rotary evaporator flask. The rotary evaporator was operated at 70° C. under vacuum to remove the hexane from bio-crude. Bio-crude weight was calculated after subtracting the flask weight and was then transferred into sample vials. Bio-crude samples were preserved at −5° C. until analyzed to prevent oxidation. After analysis, bio-crude samples were purified through an activated charcoal bed with hexane as eluent to obtain pure algal oil. The pictures of algal bio-crude and pure algal oil are shown in FIG. 6. All the optimization experiments were replicated five times for consistency of the results and the average values of these replicates with standard deviation are reported herein. The extraction of bio-crude calculations were performed using the formulae given below $$\text{Bio-crude yield} = \frac{\text{weight of bio-crude extracted}}{\text{dry weight of biomass}} * 100$$

$$\text{FAME yield in bio-crude} = \frac{\text{weight of FAMEs}}{\text{weight of bio-crude}} * 100$$

$$\text{FAME\% extracted} = \frac{\text{Avg. weight of FAMEs in bio-crude}}{\text{dry weight of biomass}} * 100$$

$$\text{Extraction efficiency} = \frac{\text{Avg. Amount of FAMEs extracted}}{\text{FAMEs content of biomass (dry basis)}} * 100$$

Both the SCW and MW-SCW extraction methods were carried out according to the design of tests, and process parameters were optimized for maximum bio-crude extraction. The optimized process parameters were taken as standard process parameters for the final experiments and the extraction results were compared to the conventional solvent extraction method i.e., Folch extraction.

Figure 2:
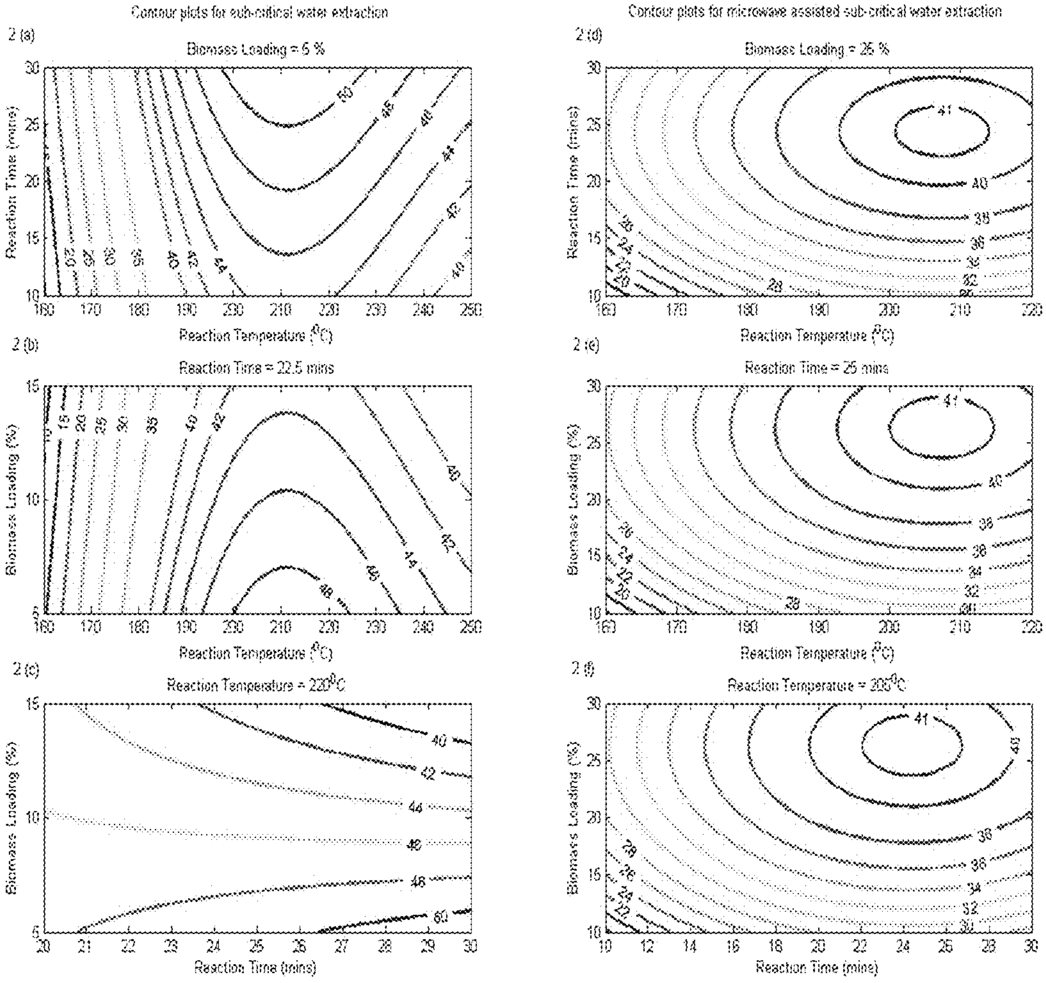
FIG. 2 shows contour plots of experimental parameters on bio-crude.

Based on the preliminary test results, a central composite design and results as shown in Table 1 were used to study the effect of extraction temperature (156° C.-250° C.), extraction time (10-35 min.), and biomass loading (3-11.7%) on bio-crude yield in order to optimize the extraction parameters. The contour plots of results shown in FIG. 2 demonstrate the influence of the parameters. Extraction temperature is an influencing factor on bio-crude extraction, which varies the polarity of the water. FIG. 2*a* shows that extraction yield is increased with the increase in the temperature until it crosses the optimum region border; and this is attributed to the increased polarity of water. The increased polarity of water at this temperature is caused by breaking of hydrogen bonds between water molecules that increases the miscibility between lipids and water. This property of water also makes the separation very easy when the process temperatures are reduced to room temperature. The yield of bio-crude is decreased beyond the optimum region with increase in temperature. Hydrolysis is the predominant reaction in this region of temperature, and we wanted to extract neutral lipids in their original form, so we chose the lower temperature 220° C. as optimum temperature. Hydrolysis of polysaccharides and cellulose compounds happens in this same range, which formed small water soluble compounds and further increase in temperature beyond 260° C. caused a repolymerization reaction of these water soluble compounds to form oil products, which increased the bio-oil yield. Hydrolysis of TAG's was observed at 240° C. in preliminary experiments with FT-ICR analysis (data not shown).

The degradation of polyunsaturated fatty acids was observed in TGA analysis. The systematic optimization of the temperature range was established for the extraction of neutral lipids with this design, which was efficient for the extraction of the respective class of compounds. But dewatering was also an energy intensive step in algal biofuels production, therefore the biomass loading was tested as a parameter. It was found that the biomass loading was an influencing parameter in subcritical water extraction process. FIG. 2*b* shows the effect of biomass loading on the extraction of bio-crude yield. The extraction of bio-crude was increased with decreasing biomass loading and reached maximum at 5% of biomass loading. The lesser biomass loading or higher solvent ratios, i.e., water ratios increased the liquid yields possibly because of the denser solvent environment. The biomass loading was 7.5% as lower biomass loading may need higher amounts of heat energy for the extraction process.

Extraction time is the last influential parameter on extraction of bio-crude. The yield of bio-crude was increased from start of the extraction process and reached maximum around 30 min., and the effect of extraction time on bio-crude yield is shown in FIG. 2*c*. 25 min. of extraction time was selected as optimum time for extraction because extended extraction times may cause a decrease in the bio-oil yield due to secondary and tertiary reactions, e.g., hydrolysis and repolymerization, which are important factors in hydrothermal liquefaction of biomass since they convert heavy compounds into either liquids, gases or solid residues.

Microwave-Assisted Lipid Extraction

The effects of the process parameters (extraction temperature, biomass loading and extraction time) showed similar effects in MW-SCW as in conventional SCW with some changes in those effects. The central composite design which was used for the tests and results is shown in Table 2. The extraction temperature was an influencing parameter, as in the conventional heating method. The bio-crude yield was increased from 160° C. until the optimum region was reached, as shown in FIG. 2*d*. The decrease in dielectric constant or increased polarity was caused by the breaking of hydrogen bonds between water molecules at higher temperatures which increased solubility of lipids in water.

TABLE 2

| Microwave-assisted subcritical water extraction | | | | |
|---|---|---|---|---|
| Exp. run | Temp | Extraction Time (min.) | Biomass loading | Yield (%) of bio crude(dry wt. basis) |
| 1 | 185.00 | 10.00 | 30.00 | 22.51 |
| 2 | 185.00 | 20.00 | 10.00 | 23.68 |
| 3 | 167.50 | 10.00 | 30.00 | 24.07 |
| 4 | 168.00 | 20.00 | 30.00 | 25.71 |
| 5 | 185.00 | 30.00 | 10.00 | 25.87 |
| 6 | 220.00 | 10.00 | 20.00 | 26.58 |
| 7 | 220.00 | 10.00 | 30.00 | 27.71 |
| 8 | 168.00 | 30.00 | 30.00 | 29.60 |
| 9 | 185.00 | 30.00 | 20.00 | 34.36 |
| 10 | 220.00 | 30.00 | 20.00 | 34.78 |
| 11 | 185.00 | 20.00 | 20.00 | 36.35 |
| 12 | 185.00 | 30.00 | 30.00 | 36.84 |
| 13 | 220.00 | 30.00 | 30.00 | 38.17 |
| 14 | 185.00 | 20.00 | 30.00 | 39.05 |
| 15 | 220.00 | 20.00 | 20.00 | 39.37 |
| 16 | 220.00 | 20.00 | 30.00 | 39.51 |

In the microwave-assisted heating method, the heat and mass transfers occurred in the same direction, i.e., from the sample to the solvent medium, but in conventional heating the heat energy is transferred from the medium to the sample biomass and mass transfer occurs from sample biomass cells to the outside medium. The heat transfer mechanism in conventional heating depends on the thermal conductivity of the sample and solvent; convective currents make it a slow process, where in microwave heating, due to the volumetric heating, the heat transfer process is very fast and rapid.

Another influencing parameter besides temperature is biomass loading. Differing with the conventional heating method, in the microwave heating method the yield of bio-crude is increased with increasing biomass loading from lower amounts. The contour plot in FIG. 2*e* shows that the extraction is preferably achieved at between approximately 25 and approximately 29% biomass loading. The higher amount of solvent may decrease the extraction yields because of the less stirring of the solvent by microwaves. Higher solvent volumes decreasing the probability of the microwaves penetrating through the biomass is likely the reason for the decrease in extraction yields at lower biomass loading.

Extraction time is another influencing parameter on the microwave-assisted bio-crude extraction. FIG. 2*f* shows that the bio-crude yields are increased with an increase in time through the optimum region, but further increase in extraction time decreased the bio-crude yield. The degradation of thermo labile compounds might be the reason behind the decrease of the extraction yields. As discussed in conventional heating method, the secondary and tertiary reactions seem to be another reason for the decrease in bio-crude yield at prolonged extraction times.

C-SCW appears promising for extracting neutral lipids within existing industrial infrastructure. The major obstacles for scale-up of microwave systems are low penetration depth of microwave radiation, which creates thermal discontinuity throughout the reactor. By using high power magnetrons, this problem can be overcome.

Figure 3:
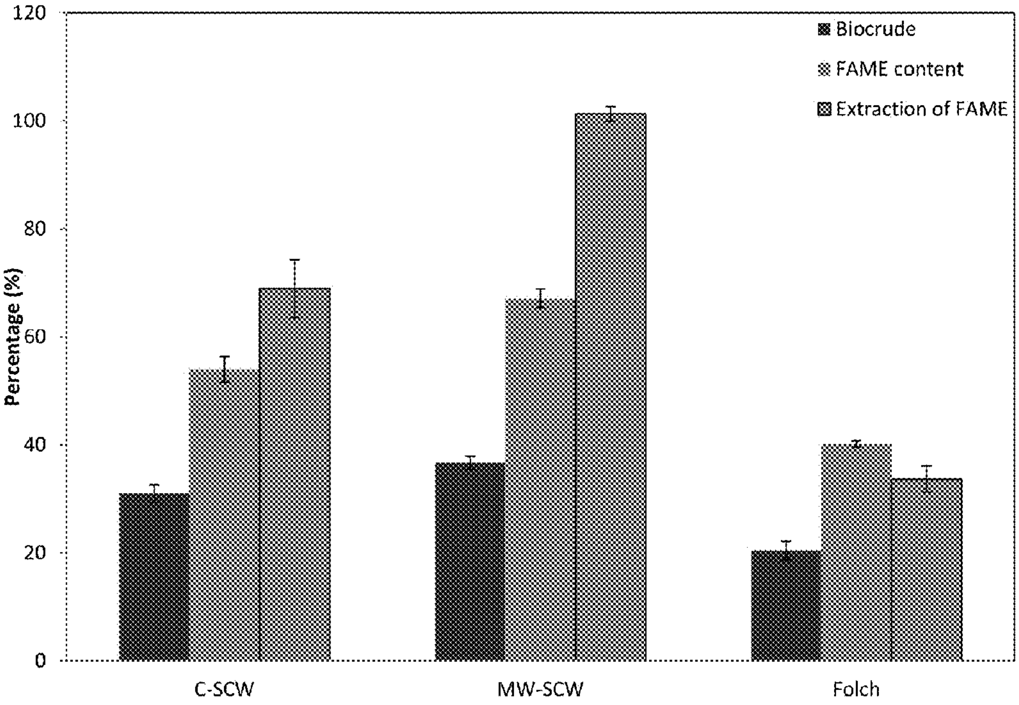
FIG. 3 shows results of yields of bio-crude, fatty acid methyl esters (FAME) content in bio-crude and extraction efficiencies obtained through embodiments of the present invention.

This research was intended to achieve maximum extraction of neutral lipids with less energy spent for extraction. For that, subcritical water extraction methods were compared to established Folch extraction method in terms of their extraction efficiencies based on the total FAME content of a direct transesterification of the algal biomass. The experimental results are an average of five replicates data under the same conditions. Both the C-SCW and MW-SCW extractions displayed higher bio-crude yield (as determined by FAME quantitation and gravimetric measurement) than the Folch extraction method. Among the three methods, the MW-SCW method extracted more bio-crude and maximum FAME content. The conventional SCW extraction is able to extract nearly 70% of the FAME content from the wet algal biomass. The conventional Folch extraction is able to extract only 33% of FAME compounds present in the algae. The yields of the bio-crude and FAME content extracted in the three methods are shown in FIG. 3. The extraction results obtained in two methods are given in Table S3 below.

TABLE S3

Extraction calculations of Folch, conventional SCW and MW-SCW methods

| | Folch Extraction | Conventional-SCW extraction | Microwave-SCW extraction |
|---|---|---|---|
| Avg. Total lipid or Bio-crude extraction (% dry wt. basis) | 20.39 ± 1.74 | 31 ± 1.6 | 35.7 ± 1.18 |
| FAME content in extracted total lipid or bio-crude extraction (% bio-crude) | 40.15 ± 0.59 | 53.99 ± 2.35 | 67.10 ± 1.74 |
| Total FAME extracted (% dry wt.) | 8.18 ± 0.59 | 16.75 ± 1.30 | 24.61 ± 0.33 |
| Extraction efficiency of FAME's | 33.65 | 68.9 | 101.2 |

Through the SCW extraction methods, the main energy consuming factor in algal biofuels is eliminated by processing wet algal biomass.

After extracting the bio-crude, the remaining lipid extracted algae (LEA) is also an important byproduct that needs to be quantified. These material balances have been taken from small volume batch experiments and expanded for 1 kg dry biomass. The bio-crude, LEA, and water were collected from each experimental run for consistent numbers. The gas phase was suspected to be predominantly $CO_2$, and the numbers were taken as the remaining amount of material after adding three products but needed to be quantified or verified. Along with LEA, the water-soluble compounds also formed considerable amounts of mass in the process. The material balances of the sub critical extraction through two methods are tabulated in Table 3 below.

TABLE 3

| | Bio-crude (g) | LEA (g) | Water soluble compounds (g) | Gaseous products (g) | Calorific value (MJ/Kg) | Crude protein % |
|---|---|---|---|---|---|---|
| C-SCW | 31 ± 1.6 | 27 ± 1.3 | 39 ± 0.9 | 2.83 ± 1.3 | 24.94 | 45.6 |
| MW-SCW | 35.7 ± 1.18 | 12 ± 1.1 | 51.2 ± 1.7 | 0.2 ± 1.2 | 21.9 | 28.5 |

The amount of LEA and water soluble compounds greatly varied in the two methods. In both methods, the water-soluble compounds were extracted more than the bio-crude, but these numbers had a large difference between both methods. As shown in Table 3, in the conventional heating method more LEA biomass was retained compared to the MW-SCW method. This could be a result implicated from the direct heating of the biomass through the water medium in the later method; the reaction temperature was achieved by microwave heating. In an opposite manner, more water soluble compounds were extracted in MW-SCW than the conventional heating method. The preliminary nutrient analysis and calorific values of LEA also prove that MW-SCW had extracted most of the compounds both in bio-crude and water phase.

The freshly harvested *N. salina* from photo bioreactors was analyzed for its fatty acid profile by direct FAME method described above. The major fatty acids detected were hexadecanoic acid, C16:0 (29.71%); hexadecenoic acid, C16:1n7 (41.91%); cis-9-Octadecanoic acid, C18:1n9c (9.9%); cis-5, 8,11,14,17-eicosapentenoic acid, C20:5n3 (6.78%) along with small fractions of other fatty acids. Qualitative elemental composition of the fresh biomass and LEA biomass were carried by a SEM-EDS micro analysis system. The major elements detected in the samples were carbon, oxygen, sodium, magnesium, phosphorous, chlorine, potassium, calcium, and sulfur as tabulated in Table 4.

TABLE 4

| % of elements | Fresh algae | SCW | MW-SCW |
|---|---|---|---|
| C | 79.38 | 86.79 | 78.70 |
| O | 17.76 | 11.21 | 18.33 |
| Na | 0.67 | 0.12 | 0.61 |
| Mg | 0.12 | 0.09 | 0.14 |
| P | 0.10 | 0.38 | 0.22 |
| S | 0.38 | 0.28 | 0.35 |
| Cl | 0.87 | 0.13 | 0.67 |
| K | 2.37 | 0.00 | 0.32 |
| Ca | 0.21 | 0.94 | 0.66 |

Figure 4:
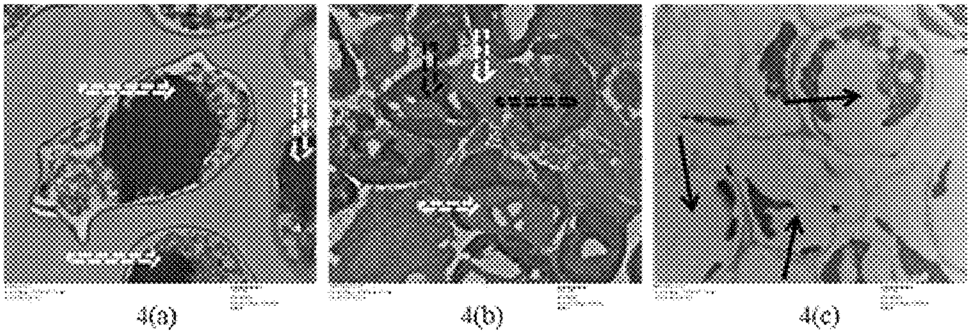
FIG. 4 shows transmission electron microscopy (TEM) images of algal biomass (a) Fresh algal biomass; (b) conventional subcritical water (SCW) lipid extracted algae (LEA); and (c) microwave-assisted subcritical water (MW-SCW) LEA.

The LEA samples revealed that there was an increase in carbon and decrease in oxygen content in biomass after extraction in conventional heating method, which was caused by the hydrothermal carbonization of the biomass. In the MW-SCW method, the exact opposite results had been found, where the LEA has less carbon and more oxygen than the former method. This behavior was also observed in TEM analysis of biomass before and after extraction. In freshly harvested biomass, the lipid globules were observed inside the biomass and marked with white dashed arrows in FIG. 4*a*. In the conventional heating SCW method, some of the lipid particles were observed outside the cell walls and between the cells which shown in FIG. 4*b*, which meant that they required further separation. The lipid globules were marked with black dashed arrows and algal char was marked with white dashed arrows. This is likely because of the strong adsorbing nature of LEA, which seems like charcoal. But in case of the LEA from the MW-SCW method, there were only a few organelles present inside the algal cells showed in FIG. 4*c*, and the empty space created inside the cells is marked with black arrows. This is the indication of the extraction capacity of both bio-crude and water soluble compounds in the MW-SCW method.

Figure 7:
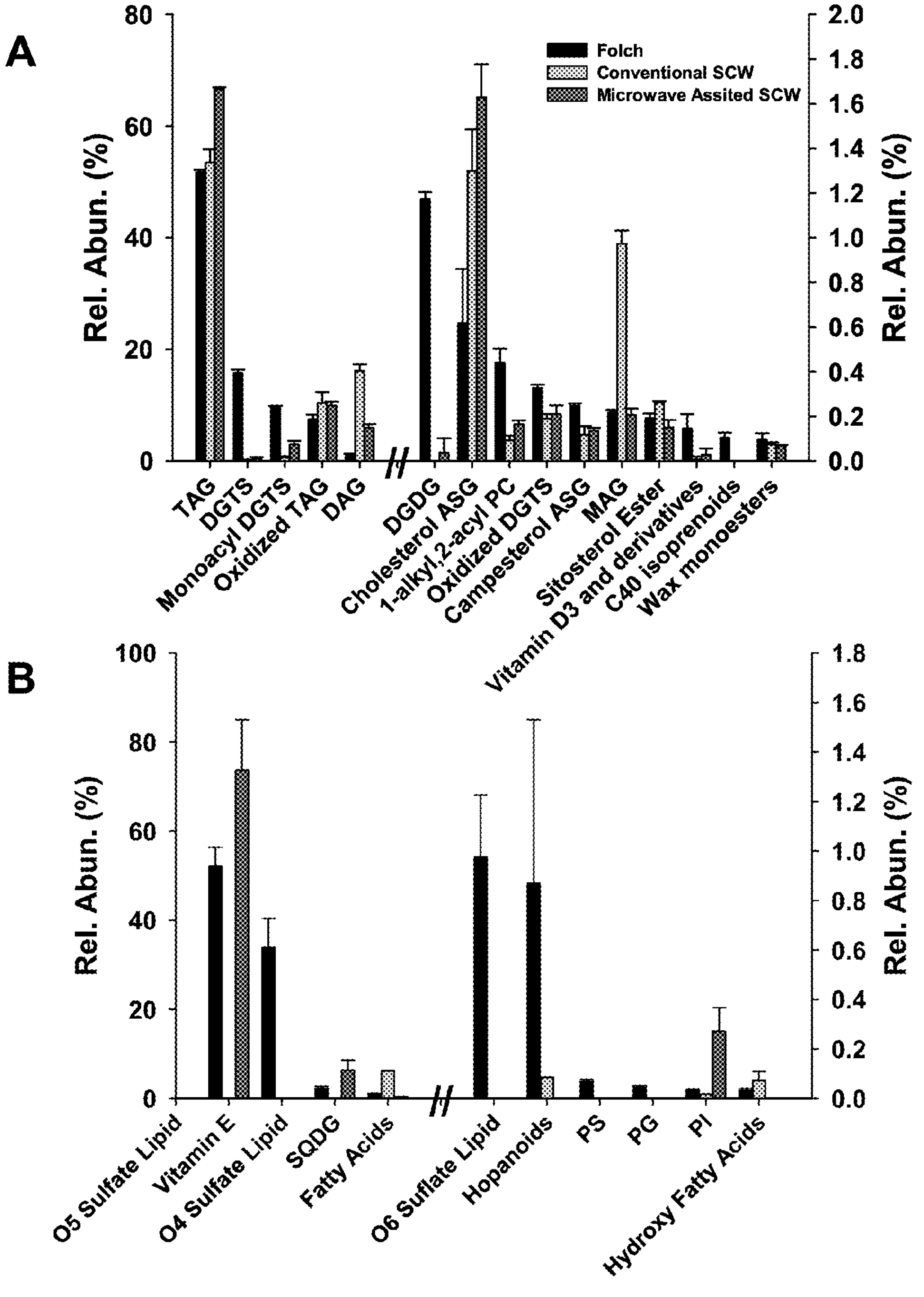
FIG. 7 shows Fourier transform ion cyclotron resonance (FT-ICR) analysis of lipid extracts (a) positive ion electrospray ionization (ESI), and (b) negative ion.
Figure 8:
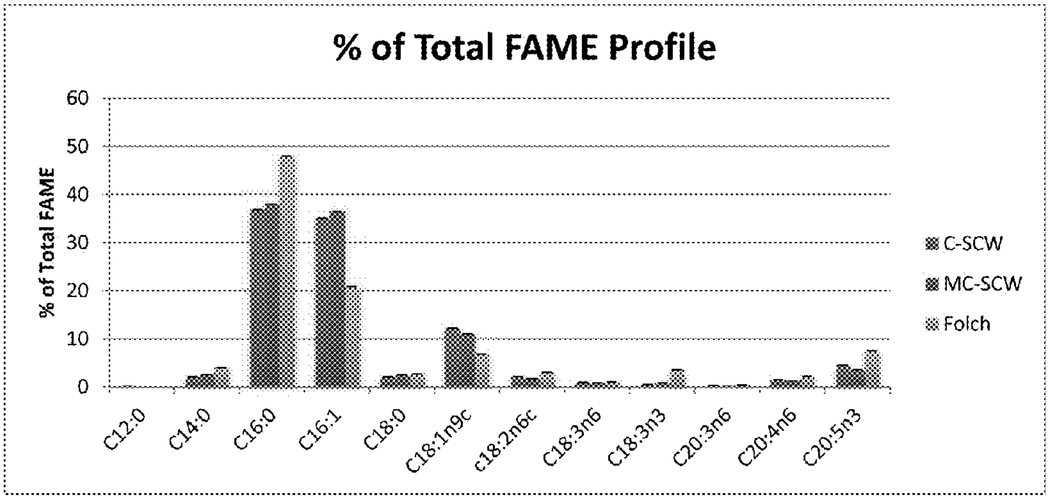
FIG. 8 is a graphical representation of the fatty acid profiles of bio-crude from conventional subcritical water (C-SCW) and MW-SCW, and Folch extractions.

Bio-crude samples extracted at optimum conditions both in conventional SCW extraction and MW-SCW experiments were analyzed with GC-MS for fatty acid profile and FT-ICR for lipid profile. The total lipids extracted in Folch extraction were also analyzed and compared to the SCW methods. The fatty acid profiles of bio-crude samples obtained in each method at optimized conditions, along with Folch extraction, were shown in FIG. 8. The intact lipid distribution acquired by FT-ICR MS (FIG. 7*a*) shows distinctly that the SCW water methods are relatively deficient in polar lipids such as 1,2-diacylglyceryl-3-O-4'-(N,N,N-trimethyl)-homoserine (DGTS), mono and digalactosyldiacylglyerols (MGDG, DGDG), phosphotidylcholines (PC), phosphotidylserine (PS) and phosphotidylglycerols (PG). The Folch extracts showed greater diversity of lipid species, while both SCW extraction methods indicate an enrichment of triacylglycerols. The conventional SCW method showed an increase of di- and monoacylglycerols. The increased ratio of DAG to TAG indicated partial hydrolysis of glycerol lipid acyl chains under these conditions. The analysis of the negative ion mass spectra supported the observation of hydrolysis by detection of free fatty acids (FIG. 7*b*). Both SCW methods also showed an increase in cholesterol acylated sterol glycoside (ASG) which has been shown to be problematic in biodiesel generated from the incomplete transesterfication of ASG, as well as sterol glycosides (SG), and sterol esters (SE). The MW-SCW extraction showed higher amounts of phosphotidylinositiol (PI) and vitamin E than either the conventional SCW or solvent based Folch extraction. Of interesting note is limited detection of C40 isoprenoids in the both the MW-SCW and SCW extracts.

Figure 5:
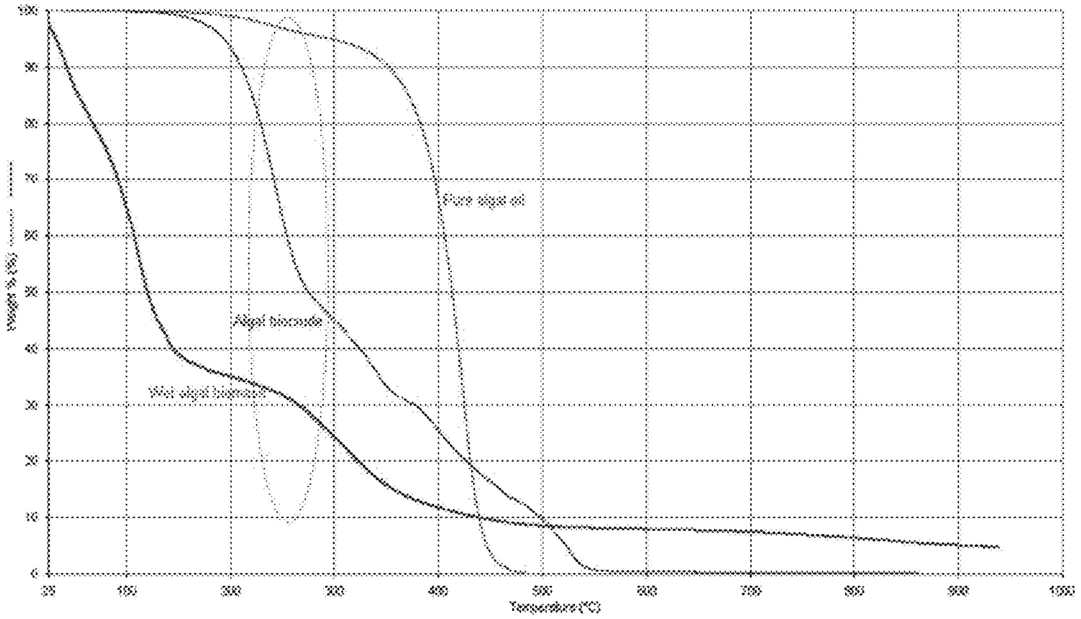
FIG. 5 shows thermogravimetric analysis (TGA) plots of wet algal biomass, bio-crude and pure algal oil.

Thermo gravimetric analysis (TGA) of wet algal biomass, bio-crude and purified algal oil was performed to analyze the thermal behavior of biomass, bio-crude, and algal oil. The samples were heated from 25° C. to 950° C. at a constant heating rate of 10° C./min in a nitrogen atmosphere, and at a constant purge rate of 20 mL/min at the pan. The linear plots of TGA for wet algal biomass, bio-crude, and pure algal oil are shown in FIG. 5.

The biomass underwent three phases of weight loss, one between 100-140° C., the second at 250° C.-300° C. and a third loss around 350° C.-500° C. The first shift represents weight loss caused by dehydration of the biomass sample. Nearly 60-65% weight was reduced in the first shift of physical change representing evaporation of water content in the sample. The second and third weight shifts were attributed to losses of organic compounds and decomposition of the algal biomass. Apart from biomass, the bio-crude missed the first shift of weight loss and did not have any incombustible material as it has only the extracted compounds. The last and third plot of pure algal oil is similar to regular vegetable oils and the only difference is a small weight loss between 250° C.-300° C. The thermal behavior of pure algal oil is close to the camelina oil and matched with crude algal lipids. As mentioned earlier, the polyunsaturated fatty acids present in the algal biomass were degrading in this range, and it can be observed in all three samples. The dotted circle shows this phenomenon in algal biomass, bio-crude and in pure algal oil and can be attributed to degradation of polyunsaturated fatty acids in the samples.

The development of valuable byproducts can help the sustainable production of algal biofuels. One valuable byproduct is eicosapentaenoic acid (EPA), which is an omega-3 fatty acid with medicinal applications like treatment of certain coronary heart disease, blood platelet aggregation, and abnormal cholesterol levels. In our conventional SCW process, the EPA is in the form of free fatty acids which can be easily separated before the conversion of algal oil into fuels. The LEA had nearly 23.4% of FAME content after extraction and 45.6% of crude protein in conventional SCW. This high amount of FAME content can be separated to produce more oil which increases the overall extraction efficiency. The potential ways of utilizing the residual FAME content in the LEA include but are not limited to conventional combustion, pyrolysis, gasification and an additional step of subcritical water extraction at different conditions. Combustion of LEA converts the FAME and other energy-containing components in LEA into thermal energy, pyrolysis produces both liquid and gas fuels from LEA, and gasification mainly produces gaseous fuel from LEA. A more efficient way of utilizing the FAME in LEA is to perform another step of subcritical water extraction of the residual FAME in the LEA. The subcritical water extraction of the residual FAME in LEA comprise higher temperatures (300-400° C.) and pressures (80-200 bar) than the first step of subcritical water extraction because the residual FAME molecules are larger and heavier.

The LEA produced from MW-SCW had 28.5% crude protein. The LEA had very high amounts of crude protein after extraction, which makes it a good animal feed source. Otherwise, the recoverable protein can be extracted for commercial human food applications as per the demand. The LEA can also be fired along with coal in power generation because of their higher calorific values. The gasification of the LEA could be used to make syngas, which can be further converted into valuable industrial chemical products. The other applications are water purification and soil remediation. Initial experiments of biosorption of arsenic with LEA (algal char) showed promising results. Last but not the least the residual water, which contains hydrolyzed organic compounds, should be analyzed for potential applications and needs to be analyzed thoroughly.

The preceding examples can be repeated with similar success by substituting the generically or specifically described reactants and/or operating conditions of this invention for those used in the preceding examples.

Note that in the specification and claims, “about” or “approximately” means within twenty percent (20%) of the numerical amount cited.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A method of lipid extraction from biomass, the biomass comprising algae and water, the method comprising:

feeding the biomass to a reactor;

pressurizing the biomass in the reactor to a pressure that is above atmospheric pressure;

heating the biomass to heat the water to a subcritical temperature and to lyse the algae in the reactor for a residency time in the reactor sufficient to lyse the algae; and separating a non-polar phase comprising greater than about 29% total lipid with a FAME content in the total lipid that is greater than about 51% for biofuel production from a polar phase comprising water and solids.

2. The method of claim 1 wherein the heating is conventional heating assisted through microwaves.

3. The method of lipid extraction of claim 2 further comprising centrifuging the biomass before feeding it to the reactor to optimize water content.

4. The method of lipid extraction of claim 2 wherein the biomass has a solids load of between approximately 0.01 dry weight percent and approximately 45 dry weigh percent.

5. The method of lipid extraction of claim 2 wherein the biomass has a solids load of between approximately 5 dry weight percent and approximately 35 dry weigh percent.

6. The method of lipid extraction of claim 2 wherein the biomass has a solids load of between approximately 15 dry weight percent and approximately 30 dry weigh percent.

7. The method of lipid extraction of claim 2 wherein the biomass has a solids load of between approximately 20 dry weight percent and approximately 28 dry weigh percent.

8. The method of lipid extraction of claim 2 further comprising recycling the water.

9. The method of lipid extraction of claim 2 wherein the subcritical temperature in the reactor is between approximately 160° C. and approximately 400° C.

10. The method of lipid extraction of claim 2 wherein the subcritical temperature in the reactor is between approximately 180° C. and approximately 280° C.

11. The method of lipid extraction of claim 2 wherein the subcritical temperature in the reactor is between approximately 195° C. and approximately 230° C.

12. The method of lipid extraction of claim 2 wherein the subcritical temperature in the reactor is between approximately 200° C. and approximately 210° C.

13. The method of lipid extraction of claim 2 wherein the residency time in the reactor is between approximately 1 minute and approximately 60 minutes.

14. The method of lipid extraction of claim 2 wherein the residency time in the reactor is between approximately 10 minutes and approximately 40 minutes.

15. The method of lipid extraction of claim 2 wherein the residency time in the reactor is between approximately 20 minutes and approximately 30 minutes.

16. The method of lipid extraction of claim 2 further comprising agitating the biomass.

17. The method of claim 2 further comprising separating fatty acid methyl esters from the solids in the polar phase.

18. The method of claim 17 wherein the fatty acid methyl esters are separated through pressurizing the biomass in a reactor to a pressure that is above atmospheric pressure and heating the biomass to heat the water to a subcritical temperature and to lyse the algae in the reactor.

19. The method of claim 18 wherein the heating is assisted through microwaves.

20. The method of claim 2 wherein a solvent is used for separating the polar and non-polar phases.

21. The method of claim 20 wherein the solvent is non-polar.

22. The method of claim 20 further comprising reusing the solvent.

23. The method of claim 2 wherein the pressure is between approximately 6 and approximately 221 bar.

24. The method of claim 2 wherein the pressure is between approximately 15 and approximately 83 bar.

25. The method of claim 2 wherein the pressure is between approximately 18 and approximately 26 bar.

26. The method of claim 1 wherein the heating is microwave heating alone.

27. The method of claim 1 further comprising separating fatty acid methyl esters from the solids in the polar phase for biofuel production.

28. The method of lipid extraction of claim 27 further comprising centrifuging the biomass before feeding it to the reactor to optimize water content.

29. The method of lipid extraction of claim 27 wherein the biomass has a solids load of between approximately 0.01 dry weight percent and approximately 40 dry weigh percent.

30. The method of lipid extraction of claim 27 wherein the biomass has a solids load of between approximately 1 dry weight percent and approximately 20 dry weigh percent.

31. The method of lipid extraction of claim 27 wherein the biomass has a solids load of between approximately 5 dry weight percent and approximately 10 dry weigh percent.

32. The method of lipid extraction of claim 27 wherein the water is recycled.

33. The method of lipid extraction of claim 27 wherein the subcritical temperature in the reactor is between approximately 160° C. and approximately 400° C.

34. The method of lipid extraction of claim 27 wherein the subcritical temperature in the reactor is between approximately 200° C. and approximately 300° C.

35. The method of lipid extraction of claim 27 wherein the subcritical temperature in the reactor is between approximately 210° C. and approximately 230° C.

36. The method of lipid extraction of claim 27 wherein the subcritical temperature in the reactor is between approximately 210° C. and approximately 230° C.

37. The method of lipid extraction of claim 27 wherein the residency time in the reactor is between approximately 1 minute and approximately 60 minutes.

38. The method of lipid extraction of claim 27 wherein the residency time in the reactor is between approximately 10 minute and approximately 40 minutes.

39. The method of lipid extraction of claim 27 wherein the residency time in the reactor is between approximately 20 minute and approximately 30 minutes.

40. The method of lipid extraction of claim 27 further comprising agitating the biomass.

41. The method of claim 27 wherein the fatty acid methyl esters are separated through pressurizing the biomass in a reactor to a pressure that is above atmospheric pressure and heating the biomass to heat the water to a subcritical temperature and to lyse the algae in the reactor.

42. The method of claim 41 wherein the heating is assisted through microwaves.

43. The method of claim 27 wherein a solvent is used for separating the polar and non-polar phases.

44. The method of claim 43 wherein the solvent is non-polar.

45. The method of claim 43 further comprising reusing the solvent.

46. The method of claim 27 wherein the pressure is between approximately 6 and approximately 221 bar.

47. The method of claim 27 wherein the pressure is between approximately 15 and approximately 83 bar.

48. The method of claim 27 wherein the pressure is between approximately 18 and approximately 26 bar.

* * * * *